United States Patent [19]  
Howe et al.

[11] 3,948,997  
[45] Apr. 6, 1976

[54] VAPOUR PHASE OXIDATION PROCESS

[75] Inventors: Brian Keith Howe, St. Albans; Francis Robert Frederick Hardy; Douglas Alfred Clarke, both of Luton, all of England

[73] Assignee: Laporte Industries Limited, London, England

[22] Filed: Mar. 14, 1974

[21] Appl. No.: 451,228

Related U.S. Application Data

[63] Continuation of Ser. No. 821,888, May 5, 1969, abandoned.

[30] Foreign Application Priority Data

May 6, 1968 United Kingdom............... 21422/68  
May 6, 1968 United Kingdom............... 21421/68

[52] U.S. Cl.............. 260/596; 260/603 C; 252/476; 260/580 P
[51] Int. Cl.².........................................C07C 45/00
[58] Field of Search...... 260/603 C, 603 HF, 593 R, 260/596

[56] References Cited  
UNITED STATES PATENTS 2,051,266 8/1936 McAllister et al.................. 260/603  
2,339,346 1/1944 McNamee et al. ................. 260/603  
3,270,062 8/1966 Merz et al.......................... 260/601

FOREIGN PATENTS OR APPLICATIONS 836,828 6/1960 United Kingdom................ 260/601  
539,030 8/1941 United Kingdom................ 260/601

Primary Examiner—James O. Thomas, Jr.  
Assistant Examiner—James H. Reamer  
Attorney, Agent, or Firm—Larson, Taylor and Hinds

[57] ABSTRACT

In the oxidation of α, β-diols to α, β-diones with oxygen, the use of a catalyst comprising at least one metal selected from Cu, Ag and Au and at least one element selected from Ge, Sn, Pb, N, P, As, Sb, Bi. In the oxidation of ethylene glycol to glyoxal with oxygen, condensing ethylene glycol from the products from the reactor and thereafter lowering the temperature to condense the glyoxal. A purification process for glyoxal uses a weakly basic anion exchange resin.

13 Claims, 3 Drawing Figures

INVENTORS
BRIAN KEITH HOWE
FRANCIS ROBERT FREDERICK HARDY
DOUGLAS ALFRED CLARKE
By Jacobs & Jacobs
ATTORNEY

VAPOUR PHASE OXIDATION PROCESS

This is a continuation of application Ser. No. 821,888 filed May 5, 1969 now abandoned.

BACKGROUND OF THE INVENTION

Dicarbonyl compounds having the carbonyl groups on adjacent carbon atoms have become particularly valuable in recent years. The quantities of the compounds that are used have increased, and continuous processes have become increasingly important. Glyoxal, in particular, has become a chemical produced in large quantities and is used in the paper industry and the textile industry. In the latter, glyoxal is used in the manufacture of resins to impregnate cellulosic fibres for the manufacture of garments and other textile goods that have "permanent press" or "easy care" finishes. High purity products are particularly desirable for these uses.

Processes that have hitherto been used for the manufacture of such dicarbonyl compounds, particularly glyoxal, involve the air oxidation of the corresponding dihydroxy compound. The oxidation is catalytic, but it will be clear to those of ordinary skill that there are many products that can be obtained by the oxidation of such dihydroxy compounds. Products that are found in substantial quantity include the hydroxy-monocarbonyl compound, and various compounds formed by carbon-carbon bond cleavage between the hydroxy-substituted carbon atoms. If either or both of the carbonyl groups of the desired product are aldehydic, the aldehydic group or groups may be oxidised to give carboxylic acid groups; for example, the products may include the α-hydroxy acids, and the α-carbonyl acids.

It is therefore important for an economic process to use a selective catalyst that gives a good yield of the dicarbonyl compound and relatively small quantities of by-product. It is also important for economic operation to produce the dicarbonyl compound with as large a conversion of dihydroxy compound for each pass through the reactor containing the catalyst as possible.

It has been proposed to use catalysts consisting of copper or of silver, or of silver and silver oxide to give the desired selective reaction conditions. The use of suppressants for undesirable reactions has also been proposed. Using these catalyst, high conversions per pass, approaching 100% result in the yields of by-products being undesirably increased. Optimisation will in general require relatively low conversions, which require recycling of the dihydroxy compound, and substantial quantities of by-products, which require separation, and are, in general, of lower value than the dicarbonyl compound and may be valueless.

It is an object of our invention to provide a process for the production of dicarbonyl compounds that gives a high conversion per pass. It is a further object of our invention to provide a process for the production of dicarbonyl compounds with low yields of by-products. It is an object of our invention to provide a process for the production of dicarbonyl compounds and for the purification thereof that produces a product of high purity. Other and further objects of our invention will be obvious to those skilled in the art from the following detailed description of our invention.

DETAILED DESCRIPTION OF THE INVENTION

Our invention provides a process for the vapor phase oxidation of a hydroxy compound to the corresponding carbonyl compound by contacting at elevated temperature a gaseous mixture containing oxygen and the said hydroxy compound with an oxidation catalyst, in which process the oxidation catalyst contains as essential constituents one or more metals of Group 1b of the Periodic Table comprising copper, silver and gold and one or more elements selected from Group IVb elements comprising germanium, tin and lead and Group Vb elements comprising nitrogen, phosphorus, arsenic, antimony and bismuth. Advantageously at least a portion of any of the Group IVb elements is present as the oxide.

Advantageously the Group Ib metal or metals is copper or both copper and silver. Advantageously the Group IVb element is tin. Advantageously the Group Vb element or elements are phosphorus or arsenic or both phosphorus and arsenic.

A particularly suitable catalyst for use in the process of the present invention contains as essential constituents either copper or silver or both and one or more element selected from tin, phosphorus and arsenic.

Particularly suitable combinations of elements that may be used in the catalyst for the process of the present invention include mixtures containing copper and phosphorus. Preferably the catalyst contains as essential ingredients copper and phosphorus, or copper, phosphorus and arsenic, or copper, phosphorus and tin.

Another preferred catalyst contains as essential ingredients copper and tin. Such a catalyst, hereinafter termed the copper-tin catalyst, preferably contains up to 40%, most preferably from 1–20%, by weight of tin at least part of which is advantageously present as tin oxide, the remainder being copper and incidental impurities.

One convenient form of the oxidation catalyst is an alloy containing all the essential constituents of the catalyst. The use of the term "alloy" in this specification and claims is not intended to exclude solutions of discrete chemical compounds, for example, copper phosphides, in a metal or metals, or mixtures of several discrete alloy phases falling with the term alloy. Advantageously the alloy is in the form of turnings, gauze or other low surface area form. Another convenient form of the oxidation catalyst is an intimate particulate mixture of the essential constituents of the catalyst, the particles being the elements themselves, or in the case of Group IVb elements additionally or alternatively an oxide of the element, or suitable alloys or compounds of the elements concerned. If the oxidation catalyst contains a Group IVb element, it may be convenient to mix an oxide thereof in a particulate form with the particles which comprise the remaining essential constituents of the catalyst. Alternatively, it may be convenient to oxidise either the surface of the alloy or the particulate element or alloy to form the metal oxide. In such a case the oxidation may conveniently be performed by contacting the alloy or element with an oxygen - containing gas at an elevated temperature. If desired, the gaseous mixture containing oxygen and the said hydroxy compound may constitute the oxygen-containing gas and oxidation of the copper-tin alloy may be effected under the process conditions employed for oxidising the hydroxy compound. Alternatively, the oxygen - containing gas may be air which is contacted with the copper-tin alloy at a temperature below the melting or sintering point of the alloy which is desirably within the range of from 400° to 550°C preferably 450° to 500°C for a period of from 1 to 6 hours. It is envisaged that oxidation of the alloy or element may also be effected by the use of other oxidisig agents capable of suitably oxidising the element on the alloy surface. For example, the copper-tin catalyst may be obtained by partial oxidation of a copper-tin alloy with nitric acid.

The catalyst may be supported, if desired, on a inorganic support material, for example pumice or alumina.

Conveniently the copper-tin catalyst may be obtained by oxidising a copper-tin alloy preferably containing up to 40%, most preferably from 1–20%, by weight of tin remainder copper and incidental impurities under conditions in which tin oxide is formed on the alloy surface.

A catalyst containing copper and phosphorus, alone or with other elements, may conveniently be manufactured using copper phosphide, either itself in particulate form, or as an ingredient used to manufacture an alloy. Desirably, the oxidation catalyst is a copper-phosphorus alloy containing up to 15% desirably from 1 to 5% by weight of phosphorus, the remainder being copper and incidental impurities. Such catalyst is conveniently obtained by alloying the required amount of copper phosphide with high purity copper.

Preferably, such a catalyst contains additionally a small quantity, for example between 0.01% and 5% most preferably between 0.1% and 0.5% by weight of arsenic. Alternatively or additionally, such a copper-phosphorus catalyst desirably contains silver suitably between 1% and 99% by weight. At the higher concentration of silver, the presence of copper aids the dissolution of phosphorus in the silver, phosphorus being very difficult to dissolve in pure silver.

The process of the invention is particularly applicable to the oxidation of diols to the corresponding dicarbonyl compounds, particularly aliphatic diols of the general formula:

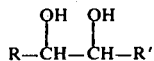

$$R-\underset{|}{C}H-\underset{|}{C}H-R'$$
$$\phantom{R-}OH\phantom{--}OH$$

wherein R and R' which may be the same or different are hydrogen or an alkyl group containing up to three carbon atoms, examples of such diols including ethylene glycol, propylene glycol and butan-2,3-diol, and alicyclic diols, for example, cyclohexan-1,2-diol.

The process of the invention is envisaged as being applicable to the oxidation of other hydroxy compounds to the corresponding carbonyl compounds, examples of such hydroxy compounds including aliphatic alcohols particulary those containing from one to six carbon atoms, alicyclic alcohols such as cyclohexanol and aromatic alcohols such as benzyl alcohol.

In the process of the invention the molar ratio of oxygen to hydroxy compound in the gaseous mixture is preferably not greater than 4:1 and is desirably about 1.3:1.

The gaseous mixture preferably contains a diluent gas for example nitrogen, carbon dioxide, steam or other gas which is preferably inert to the reactants and products under the conditions of the reaction. Suitably the molar ratio of diluent gas to oxygen is within the range from 5:1 to 200:1, desirably from 20:1 to 100:1 preferably from 40:1 to 80:1 and most preferably in the range from 40:1 to 60:1. The mixture of the diluent gas and the reaction product after the readily condensable products have been separated therefrom is hereafter referred to as "recycle gas".

The oxygen or oxygen containing gas may be introduced at one or more suitable points spaced along the reactor in which the oxidation reaction is carried out.

A reaction temperature of from 180°C to 600°C, preferably of from 300°C to 450°C, may be employed. The optimum reaction temperature for a particular run will be dependent upon the reactivity of the hydroxy compound and upon the selected operating conditions, in particular the selected time of contact of the gaseous mixture with the oxidation catalyst. In general, the shorter the selected contact time, the higher will be the optimum reaction temperature.

Suitable contact times lie within the range of from 0.1 to 20 seconds and preferred contact times within the range of from 1 to 5 seconds.

As stated the process of the invention is particularly applicable to the oxidation of diols to the corresponding dicarbonyl compounds. In this application the invention enables high yields of these compounds to be obtained with relatively low yields of by-product hydroxy carbonyl compounds.

Thus, for example, where the hydroxy compound is ethylene glycol then by the process of the invention yields of glycol in excess of 70% may be obtained with insignificant quantities of by-products glycollic aldehyde.

In the manufacture of glyoxal from ethylene glycol, incomplete conversion of ethylene glycol to oxidation products and ethylene glycol constitutes an undesirable impurity in the resulting glyoxal. To avoid unduly high concentrations of ethylene glycol it has hitherto been necessary to use oxidation conditions giving high conversions of ethylene glycol to oxidation products, preferably conversions approaching 100%. In general, however, as the ethylene glycol conversion approaches 100%, so the yield of glyoxal falls off, with the result that at very high ethylene glycol conversions the overall output of glyoxal may be undesirably low. The process using the catalyst of the present invention enables high yields of glyoxal to be obtained with high conversions of ethylene glycol. However, a further feature of the invention provides a process for separating, if desired, ethylene glycol from glyoxal.

According to this feature there is provided a process of preparing an aqueous solution of glyoxal from hot reaction gases containing glyoxal and unreacted ethylene glycol and obtained from an oxidation zone in which ethylene glycol is oxidised in the vapor phase which comprises cooling the reaction gases to a temperature below the condensation point of ethylene glycol but above the condensation point of glycol for the said reaction gases to condense the ethylene glycol, separating the condensed material so obtained, and forming an aqueous solution of glyoxal from the remaining glyoxal-containing reaction gases.

In the vapor phase oxidation of ethylene glycol to glyoxal it is customary to effect oxidation with molecular oxygen and to employ a diluent gas such as nitrogen or other gas or mixture of gases which is inert to the reactants and products. The reaction gases obtained from the oxidation zone will therefore generally contain a diluent gas and any unreacted oxygen and the condensation points of ethylene glycol and glyoxal for a particular system of reaction gases will be dependent upon the concentration of the diluent gas and unreacted oxygen in the reaction gases.

The optimum temperature to which to cool a particular system of reaction gases to effect maximum condensation of ethylene glycol consistent with minimum condensation of glyoxal can, however, be determined by experiment. For the purposes of illustration, it may be mentioned that where a mixture of ethylene glycol, oxygen, nitrogen and water in the approx. molar proportions of 1:1.2:50:1.2 respectively was employed as feed mixture to the ethylene glycol oxidation zone, 50°C was found to be a preferred temperature to which to cool the reaction gases to effect maximum condensation of ethylene glycol.

It has been found that on condensation, the ethylene glycol dissolves an approximately equivalent amount of glyoxal vapour with which it reacts to form 2:3-dihydroxydioxan. Since this compound has a lower vapour pressure than that of ethylene glycol, formation of this dioxan compound facilitates removal of ethylene glycol from the vapor phase.

In addition to 2:3-dihydroxydioxan, the condensed material obtained on cooling the reaction gases to effect condensation of ethylene glycol may contain varying amount of other high boiling point impurities which may be present in the reaction gases, for example glycollic aldehyde, glycollic acid and high boiling point coloured constituents. Thus any glycollic aldehyde may be effectively removed with the ethylene glycol, and the concentration of any glycollic acid and any high boiling point coloured constituents in the reaction gases may be substantially reduced.

It has been found that when 2:3-dihydroxydioxan, which may be dissolved in a suitable solvent such as ethylene glycol, is rapidly raised to an elevated temperature over a very short period of time, for example a few tenths of a second or less, the 2:3-dihydroxydioxan is converted in a substantially quantitative yield of ethylene glycol and glyoxal. The elevated temperature is such as to cause the 2:3-dihydroxydioxan to dissociate when the temperature is rapidly raised.

According to a further feature of the present invention, the 2:3-dihydroxydioxan obtained by condensing ethylene glycol from the reaction gases issuing from the oxidation zone, preferably dissolved in a suitable solvent such as ethylene glycol, is rapidly raised to an elevated temperature, for example 300°C, over a very short period of time such as a few tenths of a second or less, and the gaseous products so obtained containing ethylene glycol and glyoxal are recycled to the oxidation zone. A solution of the 2:3-dihydroxydioxan may be prepared by dissolving the condensed material, obtained on cooling the reaction gases to the stated temperature, in a suitable solvent such as for example ethylene glycol.

In a preferred method of rapidly raising the 2:3-dihydroxydioxan to an elevated temperature, a solution of the 2:3-dihydroxydioxan in ethylene glycol in the form of a stream of fine droplets, such as is obtained by passing the solution through a fine jet, is caused to impinge with a high velocity stream of gas such as nitrogen, or any other convenient gas, which is maintained at the elevated temperature. If desired, the high velocity stream of gas may be constituted by residual gase obtained after removal of ethylene glycol, glyoxal, and formaldehyde from the reaction gases.

In the step of rapidly raising the solution of the 2:3-dihydroxydioxan to an elevated temperature to form ethylene glycol and glyoxal, the presence of hot solid surfaces is considered to be undesirable since such surfaces facilitate undesirable resinification reactions.

Aqueous solutions of glyoxal produced by the oxidation of ethylene glycol, whether treated by cooling the reaction gases to a temperature below the condensation point of ethylene glycol but above the condensation point of glyoxal or not, may contain a small quantity of formaldehyde which is undesirable in glyoxal solution. This may be removed by purging the aqueous solution of glyoxal at an elevated temperature, advantageously from 90°C to 140°C preferably from 90°C to 105°C, with a gas. The gas may for example, be steam or it may be a mixture of steam and nitrogen. Conveniently the gas is recycle gas or a mixture of recycle gas with steam.

It will be seen that in one form, the present invention provides a particularly advantageous method for preparing and purifying an aqueous solution of glyoxal obtained by the vapour phase oxidation of ethylene glycol, in that provision is made for separating and recycling unreacted ethylene glycol and from removing oxidation by-products.

Aqueous solutions of glyoxal produced by the oxidation of ethylene glycol may also contain organic acid impurities. These may conveniently be removed, preferably after the aqueous solution has been purged with the gas, by contacting the aqueous solution with a weakly basic anion exchange resin in the free base form.

Suitably, the weakly basic anion exchange resin in the free base form is an anion exchange resin containing tertiary amino substituents such as, for example, the ion exchange resin available under the trade designation Amberlite (Registered Trade Mark) IRA-93.

Preferably, the weakly basic anion exchange resin is a macroreticular resin. Amberlite IRA-93, in which tertiary amino substituents are contained within a styrene-divinylbenzene matrix having a high surface area and large pore volume, is an example of a resin of this type.

Heretofore, it has always been supposed that basic anion exchange resins in other than a salt form would cause the glyoxal in solution to undergo a Cannizzaro type reaction and that such reaction would result in the loss of a considerable proportion of the glyoxal in the aqueous solution. Contrary to expectations it has now surprisingly been found that by the process of the invention no significant loss of glyoxal occurs. After contact with the weakly basic anion exchange resin, glyoxal recoveries of 99% have been obtained.

It has further been found that, in addition to removing organic acid impurities, the exchange resins of the invention, particularly the macroreticular resins, remove coloured impurities and also impurities which give rise to colour on standing or heating.

In carrying the invention into effect it is preferred to use aqueous solutions containing less than 50% by weight of glyoxal. At concentrations of greater than 50%, the solution becomes rather viscous and the rate of removal of organic acids falls off.

The organic acid impurities present in aqueous solution of glyoxal obtained in this manner may typically include formic acid, glycollic acid and glyoxylic acid.

The weakly basic anion exchange resin may be regenerated, when exhausted, by using aqueous alkaline solution in known manner.

Glyoxal produced by the process of the present invention is particularly suitable for conversion into the monourein of glyoxal, 4,5-dihydroxy-2-ketoimidazolidine, and the 1- and 1,3- methylol derivatives thereof and derivatives of these compounds. Since the glyoxal so produced contains less of certain impurities, for example glycollic aldehyde, than in certain other processes hitherto proposed using other catalysts, the 4,5-dihydroxy-2-ketoimidazolidine and the 1- and 1,3-methylol derivatives thereof, and derivatives of these compounds, can be prepared containing correspondingly less impurities.

4,5-dihydroxy-2-ketoimidazolidine, its 1- and 1,3-methylol derivatives, and derivatives thereof, for example O-alkyl derivatives, can be used to impregnate cellulosic fibres, for example cotton and rayon. The impregnation may be at any stage in the manufacture of garments or textile goods including stock or yarn, fabric in bulk or when out, and the made-up garment. Any cellulosic fibre may be impregnated, and blends of cellulosic fibres with non-cellulosic fibres, for example polyesters and polyamides, are not excluded.

The impregnated fibres, when in the form of garments or textile goods can be cured, using a catalyst which is conveniently impregnated into the fibres with the 4,5-dihydroxy-2-ketoimidazolidine. The curing is normally at an elevated temperature, usually less than about 240°C. When cured the garment or the textile goods retain any crease that were in the garment or the textile goods during curing. Cured garments or textile goods can be readily washed while retaining their creases or smooth finish. This is known as a "permanent pleating" or "easy care" finish.

4,5-dihydroxy-2ketoimidazolidines are manufactured from glyoxal and urea by the admixture of solutions of glyoxal and urea at a suitable pH. At low pH values, the product is 2-keto-4,5-ureyleneimidazolidine. This does not polymerise itself, but the N-methylol derivatives thereof will polymerise on curing, giving a polymer that discolours readily. At high pH values, other products that discolour rapidly are formed. As a general guide a pH of between 3 and 9 is suitable.

If the reaction to form the 4,5-dihydroxy-2-ketoimidazoline is conducted in the presence of formaldehyde, the product wll be either 4,5-dihydroxy-2-keto-1- methylolimidazolidine or 4,5-dihydroxy-2-keto-1-3-dimethylolimidazolidine or a mixture thereof. If, in addition, a lower alkanol, preferably having 1 to 4 carbon atoms, is present, the products will be the O-alkylmethylol derivatives. In such a case, it is convenient to use the lower alkanol as the solvent, or at least a substantial proportion of the solvent, in which to manufacture the 4,5-dihydroxy-2-ketoimidazolidine.

The invention will now be illustrated by way of the following non-limitative examples.

In each example relating to the oxidation process, unless otherwise specified, a reactor in the form of a glass tube of length 61 cms. and diameter 3.8 cms. was used. The reactor was electrically heated along its length in a differential manner and was packed with the specified oxidation catalyst. In each example the peak of the temperature gradient along the reactor under steady operating conditions was measured and recorded as the reaction temperature.

The terms given in the left hand column of Table 1 below have the meansings given in the right hand column of Table 1 in the headings of Table 2 and 3 below.

Table 1

| | |
|---|---|
| Catalyst | In each case given as % by weight composition of the elements stated. |
| Temp. | Maximum temperature in the reactor in °C |
| Reactant ratio | Molar ratio of reactants and diluent gases, in a ratio diol:$O_2$:$N_2$:$H_2O$ |
| Conversion | % of diol oxidised |
| Yield | % of diol oxidised which formed the stated product on a molar basis. |
| Flow | Rate of flow of reactants through the reactor expressed in liters (at 20°C/min. and atmospheric pressure |
| None | No compound detected. |

EXAMPLE 1

This example illustrates the process of the invention as applied to the oxidation of ethylene glycol to glyoxal using an oxidation catalyst obtained by oxidising a copper-tin alloy or a copper-tin-phosphorus alloy or a copper phosphorus alloy of stated composition.

The conditions employed and the results obtained in a series of runs are shown in Table 2.

In run 2, the stated alloy was a commercially available material in the form of 30 mesh gauze coils of length 1.2 cms. and diameter 0.6 to 1.0 cms. In the other runs, the alloy was in the form of turnings and was prepared by alloying together the required amounts of tin, copper and, for the phosphorus containing alloys, copper phosphide. Both the copper and tin components were of purity greater than 99.99%.

For each run the surface of the specified alloy was activated by an oxidation treatment under the conditions subsequently employed for the oxidation of ethylene glycol except that no ethylene glycol is present during the activation period. The activity of the catalyst reached a maximum in 2 to 3 hours in the case of alloys containing phosphorus and in 40 to 60 hours where phosphorus was absent and thereafter remained substantially constant. For run 2 there was no decline in catalyst activity after 320 hours of producing glyoxal. X-ray examination of the catalysts containing tin in their activated state showed that tin dioxide was present on the catalyst surface.

TABLE 2

| Run No. | Catalyst | | | Reactant Ratio | Flow | Temp. | Conversion | Yield $(CHO)_2$ | Yield $CHO.CH_2OH$ |
|---|---|---|---|---|---|---|---|---|---|
| | Cu | Sn | P | | | | | | |
| 1 | 95 | 5 | — | 1.0:1.2:50:1.1 | 13.5 | 365 | 85 | 53 | 18 |
| 2 | 94.8 | 4.8 | 0.2 | 1.0:1.2:45:1.1 | 11.7 | 375 | 85 | 75 | < 1 |
| 3 | 80 | 20 | 0.01 | 1.0:1.3:59:1.1 | 10.6 | 360 | 92 | 55 | 11 |
| 4 | 94.1 | 4.9 | 1.0 | 1.0:1.3:59:1.1 | 9.0 | 400 | 100 | 61 | None |
| 5 | 97.5 | 2.5 | — | 1.0:1.3:47:1.1 | 12.5 | 370 | 83 | 45 | 15 |
| 7 | 98.6 | — | 1.4 | 1.0:1.2:47:1.1 | 12.2 | 392 | 89 | 76 | None |
| 8 | 98.6 | — | 1.4 | 1.0:1.6:53:1.1 | 13.3 | 430 | 97 | 62 | None |
| 9 | 98.6 | — | 1.4 | 1.0:1.4;44:1.1 | 13.2 | 457 | 100 | 55 | None |
| 10 | 97.7 | — | 2.3 | 1.0:1.2:46:1.1 | 12.0 | 421 | 96 | 72 | None |
| 11 | 97.7 | — | 2.3 | 1.0:1.1:43:1.1 | 11.7 | 418 | 98 | 70 | None |

TABLE 2-continued

| Run No. | Catalyst | | | Reactant Ratio | Flow | Temp. | Conversion | Yield (CHO)$_2$ | Yield CHO.CH$_2$OH |
|---|---|---|---|---|---|---|---|---|---|
| | Cu | Sn | P | | | | | | |
| 12 | 97.7 | — | 2.3 | 1.0:1.2:39:1.1 | 12.2 | 420 | 100 | 60 | None |

Yields and conversions given in Table 2 are those which were obtained with a fully activated catalyst.

For each run a 75% w/w solution of ethylene glycol in water was vaporised, preheated to about 220°C, mixed with a mixture of oxygen and nitrogen similarly preheated to 220°C and the resulting gaseous mixture passed at the stated flow rate through the heated reactor containing the oxidation catalyst. The primary purpose of the water in the gaseous mixture was to facilitate handling of the otherwise viscous product solution.

The reaction gases issuing from the reactor were immediately cooled by passing through two water cooled condensers and the condensed products analysed.

EXAMPLE 2

In this example, the oxidation catalyst was a mixture of copper powder and tin oxide supported on pumice, and the hydroxy compound was ethylene glycol.

The oxidation catalyst was prepared by mixing 600 cm$^3$ of pumice having a size between 2 mm and 0.75 mm mesh sieves with acetone to form a slurry and then adding to the stirred slurry, 90g. of copper powder passed through a 0.075 mm sieve and 5.7g. of tin oxide. The catalyst slurry was heated over a water bath to remove acetone and the resulting dried supported catalyst packed into the reactor. A 75% w/w solution of ethylene glycol in water was vaporised, preheated to 200°C, and mixed with an oxygen-nitrogen mixture similarly preheated to 280°C to give a gaseous mixture having a molar ratio of ethylene glycol: oxygen: nitrogen: water of 1.0 : 1.1 : 52 : 1.1. This gaseous mixture was passed to the heated reactor, packed with the above specified catalyst, at a flow rate, calculated at 20°C, of 9.4 liters per minute. No induction period was observed. The reaction temperature was 380°C.

The conversion of ethylene glycol to oxidation products was 79% and the molar yields of glyoxal and glycollic aldehyde, based on the ethylene glycol reacted, were 46% and 14% respectively.

EXAMPLE 3

This example is a comparative example in which ethylene glycol was oxidised under conditions similar to that employed in Example 1, except that the catalyst was a pure copper catalyst.

The catalyst was a copper gauze having a 0.75 mm mesh in the form of coils of length 1.2 oms. cms. the diameter of from 0.6 to 1.0 cms. The copper was of 99.95% purity. The apparatus and process employed were substantially as described in Example 1.

The molar proportions of ethylene glycol: oxygen: nitrogen: water in the gaseous mixture were 1:0 : 1.7 : 57 : 1.1 and this gaseous mixture was passed through the heated reactor containing the copper catalyst at a flow rate, calculated at 20°C, of 5.2 liters per minute. The reaction temperature was 305°C.

A conversion of ethylene glycol to oxidation products of 89% was obtained with molar yields of glyoxal and glycollic aldehyde, based on the ethylene glycol reacted, of 31% and 38% respectively.

It will be seen that in comparison with a pure copper catalyst, a mixture of copper powder and tin oxide, as illustrated in Example 2, gives a higher yield of a glyoxal and a lower yield of by-product glycollic aldehyde.

Further, when tin and in particular phosphorus are added to copper, then from the resulting oxidation catalyst glyoxal yields of greater than 70% may be obtained with insignificant amounts of by-product glycollic aldehyde, as illustrated in Example 1.

EXAMPLE 4

This example illustrates the use of various catalysts in the process of the invention. The process was carried out as described in Example 1. All the catalysts were in the form of turnings except where stated.

The Cu/Al/N alloy was prepared as follows: 650g. of copper powder, 20g. of aluminium powder and 10g. of aluminium nitride were intimately mixed in a fused silica crucible and placed in a muffle furnace at 1250° for 10 hours. A small ingot was produced on cooling the crucible to room temperature and the final ingot was obtained by repeating the heating and cooling processes. The final ingot was turned on the lathe to produce swarf which was used as a catalyst.

The results with the various catalysts are shown in Table 3.

TABLE 3

| Catalyst | Temp. | Flow | Reactant Ratio | Conversion | Yield | | | | | |
| | | | | | (CHO)$_2$ | CHO.CH$_2$OH | CH$_2$OH.-COOH | HCHO | CO$_2$ | CO |
|---|---|---|---|---|---|---|---|---|---|---|
| Ag Pure gauze (comparative) | 373 | 4.8 | 1.0:1.3:56:1.1 | 69.9 | 26 | 16 | 2 | — | 59 | |
| | 269 | 3.4 | 1.0:1.0:38:1.1 | 91.1 | 32 | 18 | 1 | — | 43 | |
| Ag/P | 430 | 11.5 | 1.0:4.0:93:1.1 | 90.4 | 70 | 1 | 1 | 3 | 12 | |
| 99.86/0.14 | 450 | 15.1 | 1.0:2.1:53:1.1 | 98.6 | 69 | 4 | 1 | 2 | 12 | |
| | 448 | 16.2 | 1.0:3.1:56:1.1 | 99.2 | 64 | 2 | 2 | 2 | 16 | |
| Ag/Cu/P | 463 | 13.7 | 1.0:1.2:56:1.1 | 96.2 | 70 | none | 1 | 5 | 10 | |
| 89.3/9.9/0.78 | 442 | 13.8 | 1.0:1.3:62:1.1 | 99.5 | 65 | none | 1 | 4 | 29 | |
| Ag/Cu/P | 480 | 13.3 | 1.0:1.2:54:1.1 | 97.7 | 66 | none | 1 | 4 | 14 | |
| 79/19.8/1.2 | 461 | 13.3 | 1.0:1.3:62:1.1 | 99.3 | 68 | none | 2 | 8 | 15 | |
| Ag/Cu/P | 465 | 13.7 | 1.0:1.1:51:1.1 | 98.4 | 60 | none | 1 | 8 | 14 | |
| 78.2/19.6/2.2 | 485 | 13.5 | 1.0:1.2:49:1.1 | 99.7 | 55 | none | 1 | 10 | 15 | |
| Ag/Cu/P | 397 | 14.4 | 1.0:1.5:55:1.1 | 90.5 | 72 | 2 | 2 | 2 | 16 | |
| 9.9/88.6/1.5 | 420 | 14.9 | 1.0:1.9:58:1.1 | 98.6 | 71 | none | 1 | 3 | 26 | |
| | 445 | 14.5 | 1.0:1.5:59:1.1 | 100 | 60 | none | 1 | 4 | 32 | |
| Cu/As | 450 | 15.9 | 1:1.6:63:1.1 | 100 | 57 | 8 | 1 | 1 | 42 | |

TABLE 3-continued

| Catalyst | Temp. | Flow | Reactant Ratio | Conversion | Yield $(CHO)_2$ | $CHO.CH_2OH$ | $CH_2OH.-COOH$ | HCHO | $CO_2$ | CO |
|---|---|---|---|---|---|---|---|---|---|---|
| 99.6/0.4 Cu/Sb | 465 | 15.9 | 1:2.8:52:1.1 | 96.7 | 74 | <2 | 1 | <1 | 14 | |
| 99.0/1.0 | 475 | 13.9 | 1:1.7:56:1.1 | 100 | 55 | <2 | 1 | 1 | 40 | |
| 97.7/2.3 Cu/Sb | 428 | 15.5 | 1:1.5:61:1.1 | 98.2 | 55 | 6 | 1 | <1 | 30 | |
| Cu/Bi 99.2/0.8 | 420 | 10.6 | 1:1.8:65:1.1 | 85.3 | 33 | 3 | 1 | 5 | 60 | |
| 99.0/0.8/0.2 Cu/P/As | 415 | 16.0 | 1:1.3:57:1.1 | 99.1 | 66 | <1 | 1 | 3 | 17 | — |
| | 415 | 16.3 | 1:1.5:58:1.1 | 100 | 64 | <1 | 1 | 3 | 32 | — |
| Cu/Al | 460 | 17.2 | 1:1.6:57:1.1 | 98.3 | 43 | 9 | 1 | 1 | 39 | — |
| 95.1/4.3 | 460 | 18.5 | 1:1.9:63:1.1 | 96.7 | 26 | 7 | 1 | 1 | 45 | — |
| comparative | 400 | 16.8 | 1:1.2:58:1.1 | 92.7 | 39 | 21 | 1 | <1 | 43 | — |
| Cu/Au/P | 418 | 15.0 | 1:1.3:59:1.1 | 100 | 51 | <1 | 1 | 3 | 31 | 10 |
| 94/5/1 | 410 | 14.9 | 1:1.2:59:1.1 | 99.7 | 56 | <1 | 1 | 1 | 28 | 13 |
| | 390 | 15.3 | 1:1.2:61:1.1 | 99.1 | 57 | <1 | 1 | 4 | 32 | 10 |
| | 375 | 15.6 | 1:1.2:62:1.1 | 95.5 | 60 | <1 | 1 | 3 | 23 | 5 |
| Cu/Al/N | 380 | 11.9 | 1:1.5:75:1.1 | 98.5 | 47 | 2 | 1 | <1 | 31 | — |
| | 338 | 10.1 | 1:1.5:63:1.1 | 98.9 | 41 | 3 | 1 | 1 | 47 | — |
| | 425 | 9.1 | 1:1.9:75:1.1 | 99.0 | 31 | 1 | 1 | 1 | 65 | — |

EXAMPLE 5

This example illustrates the use of the process of this invention in a small continuous plant.

Ethylene glycol is fed into an electrically heated vapouriser where it mixes with air and recycle gas to give a mixture of molar composition glycol:oxygen:inert diluent 1:1.25:100. This mixture then passes into a reactor which is packed with turnings of composition 97.7% copper 2.3% phosphorus. A temperature gradient exists along the tube and the maximum temperature was 386°C. The hot gases leaving the reactor are passed into a liquid quenching section. The quench solution is crude glyoxal solution which is continuously recycled from the main collection reservoir. The crude solution collected in the main collection reservoir contains approximately 41% glyoxal, 1% organic acid (mainly glycollic), 3% formaldehyde and less than 0.8% ethylene glycol the balance being mainly water. The yield of glyoxal is 66% based on the glycol oxidised. The crude glyoxal solution is then passed down a formaldehyde stripping column, while recycle gas and medium pressure steam are passed up the column. The contents of the formaldehyde stripper are maintained at a temperature of 105°C.

The formaldehyde-free solution (containing less than 0.1% formaldehyde) is then passed through an ion exchange column containing Amberlite IRA-93 anion exchange resin in the free base form. Finally, the pure dilute glyoxal solution is concentrated in a climbing film evaporator.

The final product contains 40% glyoxal, less than 0.1% formaldehyde less than 0.2% organic acid and less than 0.8% ethylene glycol percentages being by weight. It is odourless and colourless and does not develop colour or deposit solids on prolonged storage. The overall yield of glyoxal in the pure solution is 61% based on the glycol reacted.

EXAMPLE 6

This example describes a process for working up the product prepared as in Example 1.

The reaction gases were passed to a water-cooled condenser in which the gases were cooled to a temperature below the condensation point of ethylene glycol but above the condensation point of glyoxal in the mixture. The temperature to which the reaction gases were cooled was 50°C. In this manner any unreacted ethylene glycol was substantially removed from the reaction gases together wit any glycollic aldehyde, high boiling point coloured materials, and, in-part, glycollic acid. On condensing, the ethylene glycol reacted with an equivalent amount of glyoxal vapour to form 2.3 dihydroxydioxan which together with other condensed impurities constituted the condensed material which was removed from the water-cooled condenser.

The exit gases from this condenser were then passed to a second water-cooled condenser maintained at a temperature below the condensation point of glyoxal, for this particular gas mixture 15°C, to effect condensation of glyoxal. With the glyoxal, water was condensed to give an aqueous solution of glyoxal containing 30% of glyoxal.

Formaldehyde was removed from this aqueous solution of glyoxal by passing the solution down a column, packed with glass helices, in countercurrent to a mixture of steam and recycle gas maintained at a temperature of about 100°C and with which the solution of glyoxal was intimately contacted. The recycle gas was the exit gas from the second water-cooled condenser which had been scrubbed with water to remove final traces of formaldehyde. The concentration of formaldehyde in the glyoxal solution was reduced by this treatment to a level of less than 0.1% w/w.

After treatment to remove formaldehyde, the solution was passed through a weakly basic anion exchange resin in the free base form to remove organic acids and remaining coloured impurities. The resin used was Amberlite (Registered Trade Mark) IRA-93. The level of organic acid in the aqueous solution was reduced to a figure of less than 0.05% w/w.

In this manner substantially colourless solutions of glyoxal of high purity were obtained.

The by-products of this purification process could be recycled. Thus the condensed material obtained in the first water-cooled condenser could be mixed with fresh ethylene glycol solution in the required proportions and passed through an atomizer and then fed to the reactor. This was achieved by passing the solution into the atomizer in the form of fine droplets which were caused to impinge with a hig velocity stream of recycle gas maintained at 300°C. Under these conditions the 2,3-dihydroxydioxan present in the solution dissociated into ethylene glycol and glyoxal in a quantitative manner in yields of greater than 95%. The gases from the atomizer were then mixed in the required proportions with fresh air feed and fed to the reactor.

EXAMPLE 7

This example illustrates the oxidation of propylene glycol according to the invention, using an oxidation catalyst obtained from a copper-tin-phosphorus alloy.

The oxidation catalyst was that specified in run 2 of Example 1.

The molar proportions of propylene glycol : oxygen : nitrogen : water in the gaseous mixture were 1.0 : 1.5 : 40 : 1.4 and this gaseous mixture was passed through the reactor containing the above specified catalyst at a flow rate, calculated at 20°C, of 3.5 liters per minute. The reaction temperature was 320°C.

At maximum catalyst activity, obtained within a few hours, the conversion of propylene glycol to oxidation products was 93% and the molar yield of methyl glyoxal, based on the propylene glycol reacted, 75%. Acetol was obtained in a molar yield of 7%.

EXAMPLE 8

This example illustrates the oxidation of butan-2,3-diol according to the invention, using an oxidation catalyst obtained from a copper-tin-phosphorus alloy.

The oxidation catalyst was that specified in run 2 of Example 1, except that prior to mixing, the constituents of the gaseous mixture were preheated to 200°C.

The molar proportions of butan-2,3-diol : oxygen : nitrogen : water in the gaseous mixture were 1.0 : 1.5 : 38 : 1.7. The gaseous mixture was passed through the reactor containing the catalyst at a flow rate of 3.3 liters per minute calculated at 20°C. The reaction temperature was 310°C.

At maximum catalyst activity, obtained within a few hours, the conversion of the diol to oxidation products was 100% and diacetyl was obtained in a molar yield of 90%. The molar yield of the corresponding hydroxyl carbonyl compound, acetoin, was 7%.

EXAMPLE 9

This example illustrates the oxidation of cyclohexan-1,2-diol according to the invention, using an oxidation catalyst obtained by oxidising, under the conditions employed for oxidising the cyclohexan-1,2-diol, an alloy in the form of turnings and having a composition of 94.0% copper 4.9% tin and 1.1% phosphorus.

The apparatus and process employed were substantially as described in Example 1. The molar proportions of cyclohexan-1,2-diol: oxygen : nitrogen : water in the gaseous mixture were 1.0 : 3.0 : 118 : 15.0 and this mixture preheated to a temperature of 250°C, was passed through the reactor containing the above specified catalyst at a flow rate of 7.16 liters per minute, calculated at 20°C. The reaction temperature was 390°C.

The conversion of cyclohexan-1,2-diol to oxidation products was 59% and the molar yield of the corresponding dione was 63%.

EXAMPLE 10

43.5 parts of 40% aqueous glyoxal solution produced by a process similar to that of Example 5, are mixed with 46.5 parts of 40% aqueous formaldehyde solution. The mixture is adjusted to a pH of 5.5 with approximately 0.5 parts of 10% aqueous sodium hydroxide. 18.6 parts of urea are stirred in. The temperature of the solution is allowed to rise to 80°C by the application of heat and by the heat generated by the exothermic reaction which takes place. The solution is maintained at 80°C for 2 hours and then cooled. The resulting product is a clear almost colourless solution of 4,5-dihydroxy-2-keto-1,3-dimethylolimidazolidine.

DESCRIPTION OF THE DRAWINGS

An apparatus and process for the production and purification of glyoxal will now be described with reference to the accompanying drawings in which:

Referring to FIG. 1, reaction gases obtained by the catalytic vapour phase oxidation of ethylene glycol in a reactor 1 and containing glyoxal and other oxidation products together with unreacted ethylene glycol and diluent gas, including water vapour, are passed to a partial condenser 2 in which the reaction gases are cooled and unreacted ethylene glycol is condensed together with other high boiling point materials. The partial condenser 2, described later with reference to FIG. 2, is maintained at a temperature below the condensation point of ethylene glycol but above that for monomeric glyoxal.

Figure 1:
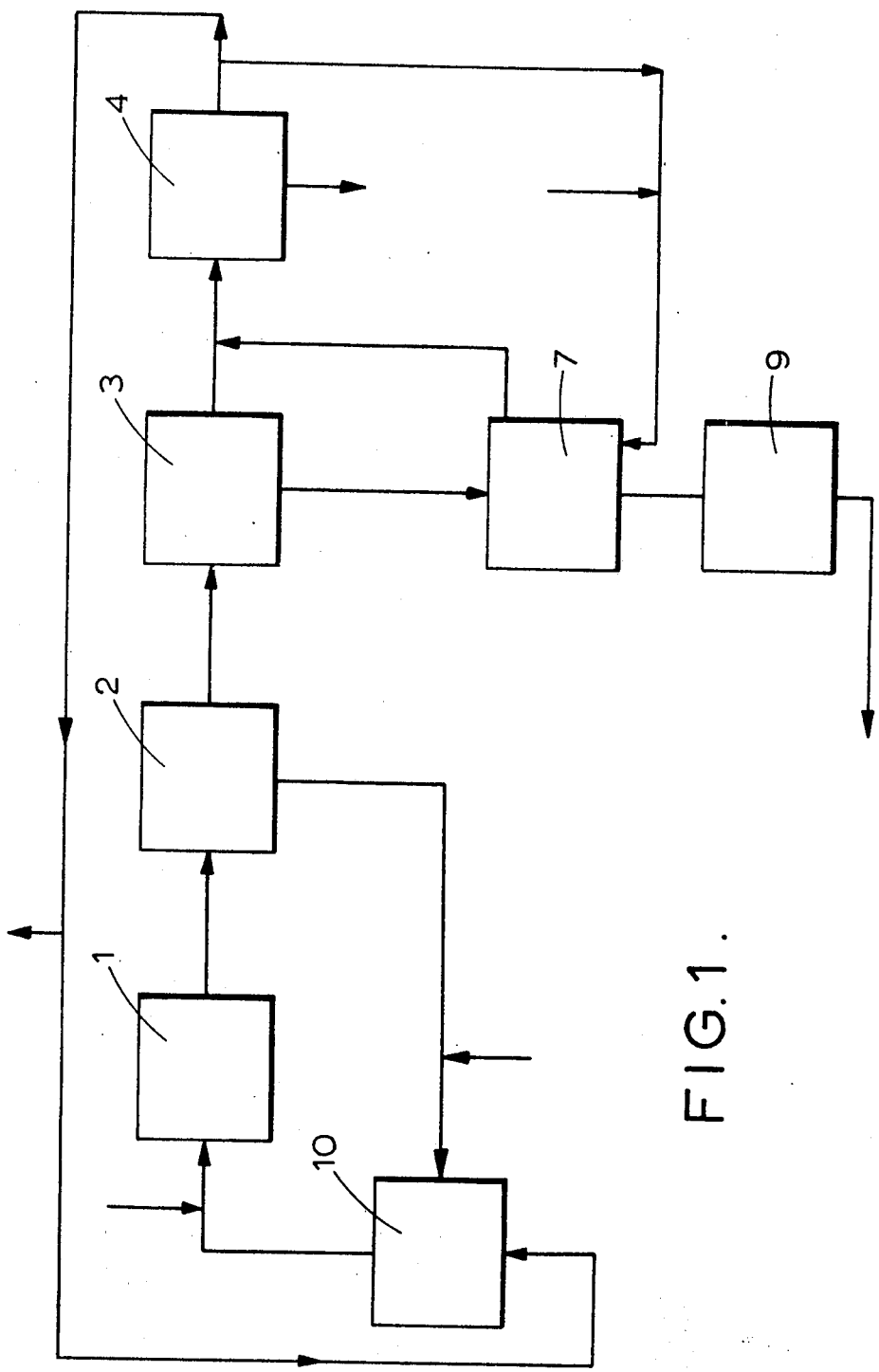
FIG. 1 is a diagrammatic layout of an apparatus in which the preparation of an aqueous solution of glyoxal and subsequent purification of the solution can be carried out.

From the partial condenser 2 the gases are passed to a water-cooled condenser 3, herein termed the glyoxal condenser, of conventional design in which the gases are further cooled to a temperature below the condensation point of monomeric glyoxal to effect condensation of glyoxal from the exit gases together with consequential water to give an aqueous solution of glyoxal. The concentration of glyoxal in the solution may be controlled, in part, by controlling the temperature of the water-cooled condenser to effect condensation of a larger or smaller quantity of water vapour. The concentration may also be conveniently controlled by adjusting the quantity of water vapour in the reaction gases. Associated with the glyoxal condenser is a conventional mist removal device, not shown, for removing fine droplets of liquid entrained in the exit gases from the glyoxal condenser.

From the mist removal device, the gases containing diluent gas, any unreacted oxygen, water vapour and traces of formaldehyde are passed to a scrubber 4 where the gases are scrubbed with water to remove the traces of formaldehyde, and then a part of the gases, constituting recycle gas, is recycled via an atomiser 10, which is described later, to the reactor 1. The other part is recycled to a formaldehyde stripper 7, as later described.

The aqueous solution of glyoxal obtained from the glyoxal condenser 3 is passed to the formaldehyde stripper 7, described later with reference to FIG. 3, in which formaldehyde is removed by contacting the solution with a gaseous mixture of steam and recycle gas. From the formaldehyde stripper 7, the solution is fed to an ion-exchange column 9, while the gaseous mixture of steam and recycle gas containing extracted formaldehyde is passed to the scrubber 4 to remove the formaldehyde and then recycled to the formaldehyde stripper 7 together with fresh steam.

The ion-exchange column 9 contains a weakly basic anion exchange resin such as Amberlite IRA-93 and on passage through this column organic acid impurities are removed from the aqueous solution of glyoxal together with coloured impurities which have not been condensed in the partial condenser 2.

Under the conditions in the partial condenser 2, ethylene glycol on condensing reacts with an equivalent quantity of glyoxal vapour to form 2:3-dihydroxydioxan and this material together with high boiling point materials such as glycollic aldehyde, various coloured materials of unknown constitution and, in part, glyollic acid make up the condensed material. The condensed material is mixed with fresh ethylene glycol and a solution is passed into the atomiser. The atomiser 10 comprises a generally cylindrical vessel having a gas inlet at one end and a gas outlet at the other end, as indicated in FIG. 1. The gas inlet is constituted by a nozzle (not shown) whose axis is aligned with the longitudinal axis of the atomiser vessel, and through this nozzle recycle gas obtained from scrubber 4 and heated to a temperature of about 300°C is passed at high velocity. A jet (not shown) is set in the side of the atomiser vessel with its axis generally normal to the axis of the nozzle and through this jet is fed the solution of the condensed material. The solution on passing through the jet is atomised into fine droplets which impinge with the hot, high velocity stream of diluent gas to cause the 2:3-dihydroxydioxan to dissociate into glyocal and ehtylene glycol.

In an alternative construction of the atomiser 10, the single jet is replaced by a plurality of jets radially spaced around the periphery of the atomiser 10.

The gas stream issuing from the atomiser 10 and containing glyoxal and ethylene glycol is mixed with air in the required proportions and passed to the reactor 1 to complete one cycle of operations.

Figure 2:
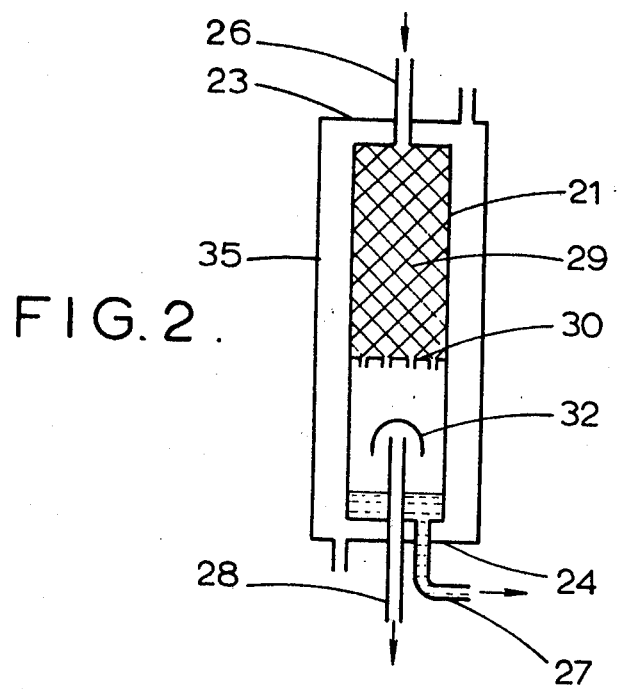
FIG. 2 is a diagrammatic elevation, in section, of a partial condenser which can be used in the preparation of the aqueous solution of glyoxal.

Referring to FIG. 2, there is shown a partial condenser of simple design which can be employed in the preparation of the aqueous solution of glyoxal.

The partial condenser comprises a cylindrical vessel 21 having a vapour inlet tube 26 in its upper end wall 23, and in its lower end wall 24, a condensate drain tube 27 and a vapour outlet tube 28. The upper part of the vessel 21 is packed with a packing 29, such as glass beads, which facilitates intimate contact between vapour and condensate. The packing 29 occupies somewhat over one half of the total volume of the vessel 21 and is supported on a support 30. The vapour outlet tube 28 extends into the lower part of the vessel 21 to a point approxiately midway between the support 30 and the end wall 24 and is provided with a cowling 32 positioned above the inlet end of the tube whose function is to prevent condensate entering the tube 28. Surrounding the vessel 21 is a water jacket 35 for maintaining the vessel 21 at the desired temperature.

In operation, reaction gases containing glyoxal, ethylene glycol and other impurities together with diluent gas, are passed into the vessel 21 which is maintained by the water-cooled jacket 35 at a temperature below the condensation point of ethylene glycol but above the condensation point of glyoxal. Ethylene glycol and other higher boiling impurities are condensed and the condensed material is withdrawn through the drain tube 27, while uncondensed vapours pass out through the vapour outlet tube 28 to be subsequently used to form the aqueous solution of glyoxal.

Figure 3:
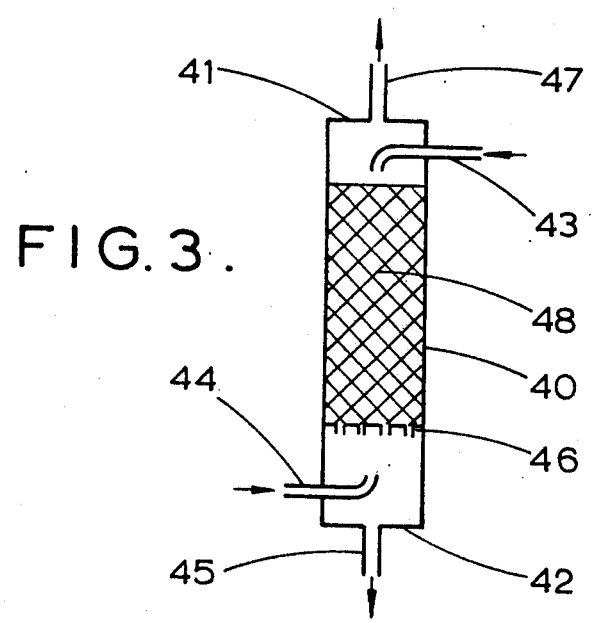
FIG. 3 is a diagrammatic elevation, in section, of a formaldehyde stripper which can be used in the purification of the solution.

Referring now to FIG. 3, there is shown a formaldehyde stripper of simple design which can be employed in purifying the aqueous solution of glyoxal.

The formaldehyde stripper shown comprises a cylindrical vessel 40 having a liquid inlet tube 43 positioned near the upper end wall 41 of the vessel 40 and extending radially inwards through the wall of the vessel towards the vessel axis, and a gas inlet tube 44 positioned near the lower end wall 42 of the vessel and similarly extending towards the vessel axis. The vessel 40 is provided with a liquid outlet tube 45 positioned in the lower end wall 42 and a gas outlet tube 47 positioned in the upper end wall 41. Above the inlet tube 44, is a plate 46 on which is supported a packing 48 of glass helices which provides intimate contact between decending liquid and ascending gas.

In operation, an aqueous solution of glyoxal containing formaldehyde as an impurity is fed into the vessel 40 through the liquid inlet 43 and passes down the vesse via the packing 48 to the liquid outlet 45. A mixture of steam and recycle gas is fed through the gas inlet 44 and passed up through the vessel to the gas outlet 47, intimately contacting the decending glyoxal solution in its passage and removing the formaldehyde impurity from the solution. The aqueous solution of glyoxal obtained at 45 is thereby substantially freed from formaldehyde impurity. In an alternative embodiment of the formaldehyde stripper, a series of plates is substituted for the packing 48, the plates being axially spaced along the length of the vessel 40 between the inlet tubes 43 and 44.

EXAMPLE 11

This Example illustrates the preparation of an aqueous solution of glyoxal from reaction gases containing glyoxal and unreacted ethylene glycol, and the purification of the solution so formed and as is described with reference to FIGS. 1 to 3.

For the purpose of this Example, the ethylene glycol feed to the reactor 1 (FIG. 1) was obtained by mixing an aqueous solution of ethylene glycol containing 75% w/w ethylene glycol with condensed material obtained from the partial condenser 2 in a previous run, and the Example will be described from this point.

A solution of the condensed material, obtained from the partial condenser 2, in a 75% w/w aqueous solution of ethylene glycol was passed to the jet, previously described, of the atomiser 10. The atomiser 10 was approximately 10 cm. in diameter and 14 cm. in length and the jet was of approximately 0.2 mm. internal diameter. The condensed material consisting primarily of 2:3-dihydroxydioxan, was fed to the atimiser 10 at a rate equivalent to 1.6 g./hr. of glyoxal and 1.7 g./hr. ethylene glycol, while the ethylene glycol constituent of the solution was fed to the atomiser 10 at a rate equivalent to 15.5 g./hr. of ethylene glycol. Recycle gas obtained from the scrubber 4 and consisting primarily of nitrogen was heated to 300°C and passed to the atomiser through the nozzle, previously described, which had an internal diameter of 1.5 mm., at a rate of 533 liters/hr. The solution of ethylene glycol and condensed material was vaporized on contacting the stream of diluent gas, and the 2:3-dihydroxydioxan converted to ethylene glycol and glyoxal in greater than 95% yield.

The gases emerging from the atomiser 10 were mixed with air and passed to the reactor 1, the quantity of air present in these gases being equivalent to 37.9 liters/hr. In the reactor 1, the gases were contacted with a bronze catalyst, in the form of gauze spirals having a weight composition of 95% copper, 4.8% tin and 0.2% phosphorus at a maximum reaction temperature of 330°C. On a molar basis, approximately 88% of the ethylene glycol was converted to oxidation products, the molar yield of glyoxal based on the ethylene glycol converted being approximately 58%.

The reaction gases from the reactor 1 were passed to the partial condenser 2, previously described, in which the cylindrical vessel 21 was 30 cm. in length and 3 cm. in diameter and which was maintained at a temperature of 50°C to condense ethylene glycol and other high boiling impurities and then to the glyoxal condenser 3, also previously described, which was maintained at a temperature of 15°C. The condensed aqueous solution obtained from the glyoxal condenser 3 contained 35% w/w glyoxal, 4.8% w/w formaldehyde, 1.7% w/w organic acids calculated as glycollic acid and 0.5% w/w ethylene glycol.

This aqueous solution of glyoxal was then fed to the formaldehyde stripper 7, which has already been described, at a rate of 5 ml./min. and contacted with a mixture of steam and recycle gas was at a temperature of approximately 100°C and was fed to the formaldehyde stripper 7 at a rate of 2 g. steam plus 1.2 liters of nitrogen per gram of glyoxal solution entering the stripper 7. After treatment in this manner, the glyoxal solution containined less than 0.2% w/w formaldehyde.

From the formaldehyde stripper 7, the aqueous solution was passed through a resin column containing Amberlite IRA-93 in the free base form at a ratio of 0.35 liters of solution per liter of resin per hour.

The effluent solution contained 20% w/w glyoxal and was concentrated to give a solution containing 40% w/w glyoxal by removing water under a reduced pressure of 12 mm. Hg. This aqueous solution of glyoxal was water-white and odourless and contained less than 0.2% w/w of formaldehyde, less than 0.02% w/w of organic acids calculated as glycollic acid and approximately 0.5% w/w ethylene glycol.

To test the tendency of this purified glyoxal solution to discolour on prolonged heating, the pH of 100 ml. of the solution was adjusted to pH 7, 10 ml. of methyl alcohol was then added and the solution boiled under reflux for 60 minutes. After treatment, the solution was almost colourless, having a Gardner reading of less than 2 units.

The purified solution did not develop a colour or deposit crystals after standing for a period of 6 months.

EXAMPLE 12

This Example illustrates the purification of an aqueous solution of glyoxal by removal of organic acid impurities present in the solution.

A column of standard design and of 0.5 liters capacity was packed in conventional manner with Amberlite IRA-93 resin in the free base form. This resin constituted the weakly basic anion exchange resin and was washed with water.

To the column was passed 235 g. of an aqueous solution of glyoxal of light yellow colour (5 Gardner units) containing 32% w/w glyoxal and 0.6% w/w organic acids calculated as glycollic acid, followed by sufficient water to elute the tail-end of the glyoxal solution from the resin. The aqueous solution of glyoxal was passed through the column at ambient temperature, flowing from top to bottom of the column, at a rate of 2 liters of solution per liter of resin per hour.

From the column, 890 g. of effluent glyoxal solution containing 8.45% w/w glyoxal was collected. The effluent solution was concentrated to give a solution containing 40% w/w glyoxal by removing water under a reduced pressure of 20 m.m Hg. This 40% w/w glyoxal solution was almost colourless (less than 2 Gardner Units) and contained less than 0.05% w/w organic acids calculated as glycollic acids. The recovery of glyoxal after treatment with the weakly basic anion exchange resin was 99%.

The resin was regenerated after a number of runs, by using a dilute slution of sodium carbonate in known manner followed by washing with water.

EXAMPLE 13

This Example illustrates the purification of an aqueous solution of glyoxal by removal of formaldehyde and organic acid impurities present in the solution.

254 g. of an aqueous solution of glyoxal of light yellow colour, 5 Gardner units, and containing 29.3% w/w glyoxal, 4.0% w/w formaldehyde and 1.4% w/w organic acids, calculated as glycollic acid, was passed to the liquid inlet 43 of the formaldehyde stripper shown in FIG. 3 at a rate of 5 ml./minute. The formaldehyde stripper was 2 cm. in diameter and 30 cm. in length and was packed with glass helices of approximately 4 mm. diameter and 4 mm. height. A mixture of steam and nitrogen at a temperature of approximately 100°C was fed through the gas inlet 44 at a rate of 2 g. of steam plus 1.2 liters of nitrogen per gram of glyoxal solution entering the formaldehyde stripper and ascended through the vessel 40 in countercurrent to the descending glyoxal solution. 232 g. of glyoxal solution of strength 32% w/w glyoxal and containing less than 0.1% w/w formaldehyde was collected from the outlet 45.

This solution was then passed to a resin column containing Amberlite IRA-93, as described in Example 12.

The effluent glyoxal solution obtained from the resin column and after concentration to 32% w/w glyoxal, containing less than 0.1% w/w formaldehyde less than 0.05% w/w of organic acids calculated as glycollic acid, and was almost colourless (less than 2 Gardner units).

The recovery of glyoxal after treatment to remove formaldehyde and organic acids was 99%.

Other and further modifications of the invention will be obvious to those skilled in the art from the foregoing description of our invention. We do not wish to be limited except by the following claims.

What we claim is:

1. In a process for the production of a dicarbonyl compound by catalytic vapour phase oxidation of cyclohexane-1,2 diol or an aliphatic diol of the formula:

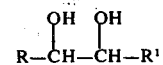

in which R and $R^1$, which may be the same or different, are hydrogen or an alkyl group containing up to 3 carbon atoms, comprising passing a gaseous mixture of oxygen and said diol at a temperature of between 180° and 600°C over an oxidation catalyst, the improvement wherein said oxidation catalyst consists essentially of one or more metals selected from a copper phosphorus alloy containing up to 15% phosphorus in the form of copper phosphide and a silver-copper-phosphorus alloy containing from 1 to 99% silver, balance copper-phosphorus containing up to 15% phosphorus in the form of copper phosphide, the catalyst optionally containing one or more elements selected from the group consisting of gold, arsenic, antimony and tin.

2. The process as claimed in claim 1 wherein the catalyst includes tin and wherein the tin is present as an oxide.

3. The process as claimed in claim 1 wherein the gaseous mixture contains a diluent gas in a molar ratio of diluent gas to oxygen of between 5 to 1 and 200 to 1.

4. The process as claimed in claim 3 wherein the molar ratio is between 20 to 1 and 100 to 1.

5. The process as claimed in claim 1 wherein the catalyst contains as essential constituents copper, tin, and phosphorus in proportions 94.8%, 4.8%, and 0.2% respectively.

6. The process as claimed in claim 1 wherein the aliphatic diol is ethylene glycol, the gaseous products of the vapour phase oxidation are cooled to a temperature below the condensation point of ethylene glycol but above the condensation poing of glyoxal, the condensed material is separated and an aqueous solution is formed from the remaining gaseous products.

7. The process as claimed in claim 6 wherein the separated condensed material is rapidly raised to an elevated temperature sufficient to convert any 2,3-dihydroxydioxane present to ethylene glycol and glyoxal.

8. The process as claimed in claim 6 wherein the separated condensed material is dissolved in ethylene glycol.

9. The process as claimed in claim 6 wherein the separated condensed material in a finely divided form is caused to impinge with a stream of gas maintained at an elevated temperature.

10. The process as claimed in claim 1 wherein the amount of phosphorus in the catalyst is at least 0.01% by weight.

11. The process as claimed in claim 1 wherein the amount of phosphorus in the catalyst is at least 0.2%.

12. The process as claimed in claim 1 wherein the amount of phosphorus in the catalyst is at least 1%.

13. In a process for the catalytic vapour phase oxidation of cyclohexane-1,2 diol or an aliphatic diol of the formula:

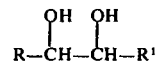

in which R and R$^1$, which may be the same or different, are hydrogen or an alkyl group containing up to 3 carbon atoms, to the corresponding di-carbonyl compound comprising passing a gaseous mixture of oxygen and said diol at a temperature of between 180° and 600°C over an oxidation catalyst, the improvement wherein said oxidation catalyst consists essentially of copper together with antimony.

* * * * *